United States Patent
Bare et al.

(10) Patent No.: US 10,039,882 B2
(45) Date of Patent: Aug. 7, 2018

(54) BINDING SYRINGE

(71) Applicant: ARTHREX, INC., Naples, FL (US)

(72) Inventors: Christopher M. Bare, Naples, FL (US); Abigail Nabors, Naples, FL (US); Melissa S. Tucker, Estero, FL (US); Robert M. Harrison, IV, Naples, FL (US)

(73) Assignee: ARTHREX, INC., Naples, FL (US)

(*) Notice: Subject to any disclaimer, the term of this patent is extended or adjusted under 35 U.S.C. 154(b) by 244 days.

(21) Appl. No.: 15/254,667

(22) Filed: Sep. 1, 2016

(65) Prior Publication Data
US 2018/0055999 A1    Mar. 1, 2018

(51) Int. Cl.
*A61M 5/19* (2006.01)
*A61M 1/16* (2006.01)
(Continued)

(52) U.S. Cl.
CPC .............. *A61M 5/19* (2013.01); *A61J 1/05* (2013.01); *A61M 1/0009* (2013.01);
(Continued)

(58) Field of Classification Search
CPC .... A61M 5/19; A61M 1/0009; A61M 1/0281; A61M 5/31511; A61M 1/3679; A61M 2202/07; A61M 2209/04; A61M 5/178; A61M 5/31; A61M 5/3145; A61M 5/34; A61M 2202/005; A61M 2202/0057; A61M 2202/0064; B01L 3/0217; B01L 2400/0475; B01L 3/0231; B01D 15/00; B01D 15/02;
(Continued)

(56) References Cited

U.S. PATENT DOCUMENTS 3,386,585 A * 6/1968 Weyand .............. A61M 5/3145
                                              210/445
4,137,917 A   2/1979 Cohen
(Continued)

FOREIGN PATENT DOCUMENTS

| EP | 0561003 A1 | 9/1993 |
| EP | 0765727 A2 | 4/1997 |
| WO | 2015/090877 | 6/2015 |

OTHER PUBLICATIONS

VWR® Syringe Filters, Polypropylene, nylon, and PTFE membranes are ideal for sample preparation and small volume chemical filtration, Retrieved on Jun. 8, 2016 from https://us.vwr.com/store/product/4830563/vwr-syringe-filters.
(Continued)

*Primary Examiner* — Joseph W Drodge
(74) *Attorney, Agent, or Firm* — McDonnell Boehnen Hulbert & Berghoff LLP

(57) ABSTRACT

A binding syringe and methods of use are disclosed. The binding syringe includes an outer body, a middle chamber, an inner body, and a plunger. The middle chamber has an outer surface including a plurality of pores, which are configured to retain certain components from biological fluid extracted by the outer body. A method of use includes placing a binding syringe into a patient or container, actuating the binding syringe to extract biological fluid, fluid flowing through a flowpath, and binding components of the biological fluid to be removed to the binding syringe.

16 Claims, 4 Drawing Sheets

(51) Int. Cl.
*B01D 15/18* (2006.01)
*A61J 1/05* (2006.01)
*A61M 1/36* (2006.01)
*B01D 61/20* (2006.01)
*A61M 5/315* (2006.01)
*B01L 3/02* (2006.01)
*A61M 1/00* (2006.01)
*A61M 1/02* (2006.01)

(52) U.S. Cl.
CPC ...... *A61M 1/0281* (2013.01); *A61M 5/31511* (2013.01); *B01D 15/18* (2013.01); *B01D 61/20* (2013.01); *B01L 3/0217* (2013.01); A61M 1/3679 (2013.01); A61M 2202/07 (2013.01); A61M 2209/04 (2013.01); B01D 2311/2626 (2013.01); B01L 2400/0475 (2013.01)

(58) Field of Classification Search
CPC .... B01D 15/10; B01D 15/1842; B01D 61/14; B01D 61/145; B01D 61/147; B01D 61/20; B01D 63/06; B01D 63/062; B01D 63/065; B01D 2311/2626; B01D 2311/2688; A61J 1/05; A61J 1/06; A61J 1/14; A61J 1/20; A61J 1/2003; A61J 1/202; A61J 1/2041; A61J 1/2044; A61J 1/2048; A61J 1/2051; A61J 1/2058; A61J 1/2079; A61J 1/2086; C12M 33/00; C12M 33/14; C12M 47/00; C12M 47/04; C12M 47/12; G01N 1/34; G01N 33/68; G01N 33/6803
USPC .. 210/321.6, 321.67, 321.87, 638, 645, 651, 210/690; 422/513, 534, 535, 546; 604/406; 436/86, 177, 178
See application file for complete search history.

(56) References Cited

U.S. PATENT DOCUMENTS

| | | | |
|---|---|---|---|
| 4,313,440 A | 2/1982 | Ashley | |
| 4,332,249 A | 6/1982 | Joslin | |
| 4,572,210 A | 2/1986 | McKinnon | |
| 5,000,854 A * | 3/1991 | Yang | A61B 5/15003 210/206 |
| 5,038,793 A | 8/1991 | Guirguis | |
| 5,470,535 A * | 11/1995 | Ray | B01D 11/0261 210/416.1 |
| 5,577,513 A | 11/1996 | Van Vlasselaer | |
| 5,902,745 A * | 5/1999 | Butler | A61F 2/022 424/424 |
| 6,589,749 B1 * | 7/2003 | Guirguis | A61B 10/007 210/321.6 |
| 6,796,965 B2 | 9/2004 | Dumaresq-Lucas et al. | |
| 8,052,969 B2 | 11/2011 | Buhr et al. | |
| 9,241,977 B2 | 1/2016 | Bare et al. | |
| 2001/0035375 A1 * | 11/2001 | Humicke-Smith | B01D 61/18 210/321.68 |
| 2003/0100125 A1 * | 5/2003 | Pressman | B01D 61/18 436/177 |
| 2003/0173284 A1 | 9/2003 | Baker | |
| 2003/0175167 A1 * | 9/2003 | Takanori | B01L 3/502 422/534 |
| 2004/0110273 A1 * | 6/2004 | Akers | C07K 14/47 435/283.1 |
| 2005/0016921 A1 * | 1/2005 | Gjerde | G01N 35/10 210/638 |
| 2007/0160998 A1 | 7/2007 | Van Beuningen | |
| 2010/0112549 A1 | 5/2010 | Rey et al. | |
| 2011/0100921 A1 * | 5/2011 | Heinrich | A61M 1/3633 210/670 |
| 2011/0124106 A1 * | 5/2011 | Froman | B01L 3/5021 435/379 |
| 2012/0164750 A1 * | 6/2012 | Gjerde | B01L 3/0275 436/178 |
| 2013/0264266 A1 | 10/2013 | Shick et al. | |
| 2015/0209502 A1 | 7/2015 | Bare | |
| 2015/0258280 A1 * | 9/2015 | Kim | A61M 5/165 604/190 |
| 2015/0283032 A1 * | 10/2015 | Lin | A61M 5/165 604/406 |
| 2015/0320938 A1 | 11/2015 | King et al. | |
| 2016/0256635 A1 * | 9/2016 | Kim | A61M 5/3145 |

OTHER PUBLICATIONS

International Search Report and Written Opinion for PCT App. No. PCT/US17/48836, dated Oct. 24, 2017.

* cited by examiner

BINDING SYRINGE

BACKGROUND

The preparation and use of biological fluids (i.e., products from blood, bone marrow, adipose tissue, etc.) can contain unwanted and in some cases detrimental cells, growth factors, and cytokines, for example. There is a need for devices and methods for selectively removing (filtering out) catabolic or deleterious factors that could impede tissue repair or remodeling from biologic products. These biologic products include protein rich plasma (PRP), autologous serum, bone marrow concentrate (BMC), bone marrow aspirate (BMA), bone marrow mononuclear cells (BMMC), stromal vascular fraction (SVF) from adipose tissue, and other enriched or concentrated biological fluids. Furthermore, it can be advantageous to isolate certain components from biologic products.

SUMMARY

This disclosure relates to devices and methods of removing unwanted and/or inhibitory components from biological fluids, and more particularly to a syringe that binds unwanted and/or inhibitory components. Also provided are devices and methods for extracting beneficial components from biological fluids, and more particularly to a syringe that binds beneficial components.

The following embodiments and aspects thereof are described and illustrated in conjunction with systems, tools and methods which are meant to be exemplary and illustrative, not limiting in scope.

In one aspect, a binding syringe is described. A binding syringe includes an outer body having a distal end and a proximal end, the proximal end having an opening for extracting fluid, and a middle chamber configured to be positioned within the outer body, the middle chamber having an open distal end, a closed proximal end, and an outer surface including a plurality of pores. The pores are configured to retain products from biological fluid extracted by the outer body. A binding syringe can further include an inner body configured to be positioned within the middle chamber, the inner body including a proximal end having a first opening and a distal end having a second opening through which the fluid flows. A binding syringe also includes a plunger configured to be positioned within the inner body, and the plunger is configured to move within the inner body, thereby pushing and pulling fluid in and out of the second opening in the inner body. A flow path is created through an opening in the proximal end of the outer body, around the middle chamber, and through the first opening in the inner body, and fluid flows within the flow path.

In another aspect, a method of extracting components of a biological fluid using a binding syringe is disclosed. The method includes placing a binding syringe into a patient or a container of biological fluid, the binding syringe including an outer body having a distal end and a proximal end, the proximal end having an opening for extracting fluid, and a middle chamber configured to be positioned within the outer body, the middle chamber having an open distal end, a closed proximal end, and an outer surface including a plurality of pores. The pores are configured to retain products from fluid extracted by the outer body. The binding syringe also includes an inner body configured to be positioned within the middle chamber. The inner body includes a proximal end having a first opening and a distal end having a second opening through which the fluid flows. The binding syringe also includes a plunger configured to be positioned within the inner body, the plunger being configured to move within the inner body. Next, a method can include actuating the plunger to extract the fluid from the patient or container, wherein a flow path is created through the opening in the proximal end of the outer body, around the middle chamber, and through the first opening in the inner body. The biological fluid flows within the flow path. Next, a method can include oscillating the plunger to bind the components of the fluid to be extracted to the pores in the middle chamber, and preserving remaining biological fluid within the flow path. Finally, a method can include injecting the remaining biological fluid back into the patient.

In another aspect, methods of extracting and recovering beneficial components of a biological fluid using a binding syringe are disclosed.

In addition to the exemplary aspects and embodiments described above, further aspects and embodiments will become apparent by reference to the drawings and by study of the following detailed description.

BRIEF DESCRIPTION OF THE FIGURES

Exemplary aspects are illustrated in the drawings. It is intended that the embodiments and figures disclosed herein are to be considered illustrative rather than restrictive.

DETAILED DESCRIPTION

A binding syringe for use with biologic fluids is disclosed. A binding syringe allows for the filtration of biological fluids like blood, serum, PRP (which can be prepared using for example, the double syringe ACP® system), autologous serum (which can be prepared using for example, an IRAP™ autologous blood processing system), BMC, BMA, BMMC, SVF from adipose tissue, and other enriched or concentrated biological fluids to remove catabolic or deleterious factors, such as proteins, that could impede tissue repair or remodeling. Proteins targeted for capture include, but are not limited to, IL-1$\beta$, IL-$\alpha$, IL-6, TNF-$\alpha$, IFN-$\gamma$, and MMPs as these proteins can inhibit the healing process. A binding syringe can also include a mechanism for binding anabolic proteins or proteins beneficial to healing, and then release those proteins after extruding the unwanted portion. Additionally, a binding syringe can be used for adipose emulsifications.

Figure 1:
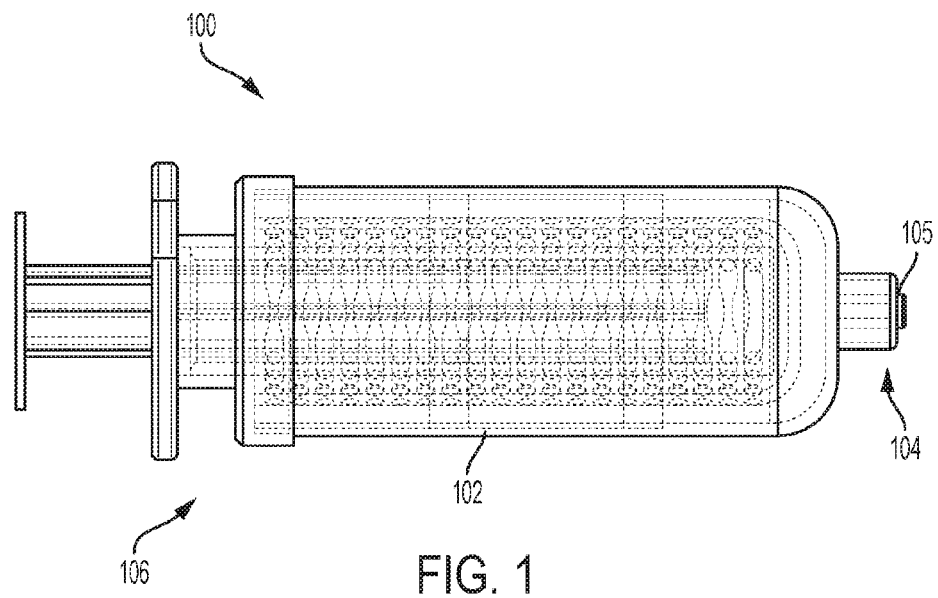
FIG. 1 is a front view of a binding syringe of the present application.

FIG. 1 shows an example binding syringe 100. In one aspect, the binding syringe 100 can be used to extract biological fluid from a patient or a container, and certain components within the fluid, such as unwanted components, bind to the syringe, thereby removing the unwanted components from the treated biological fluid. In another aspect, the binding syringe can be used to extract fluid from a patient, and anabolic proteins or other beneficial proteins can bind to the syringe. The proteins can then be released from the syringe and can then be optionally added to another source such as blood, serum, PRP, autologous serum, BMC, BMA, BMMC, SVF from adipose tissue, or other enriched or concentrated biological fluids. The beneficial proteins, optionally, in combination with blood, serum, PRP, autologous serum, BMC, BMA, BMMC, SVF from adipose tissue, other enriched or concentrated biological fluids, or other carrier, such as saline is a treated biological fluid. The binding syringe 100 and method of use are described in more detail below.

Figure 2:
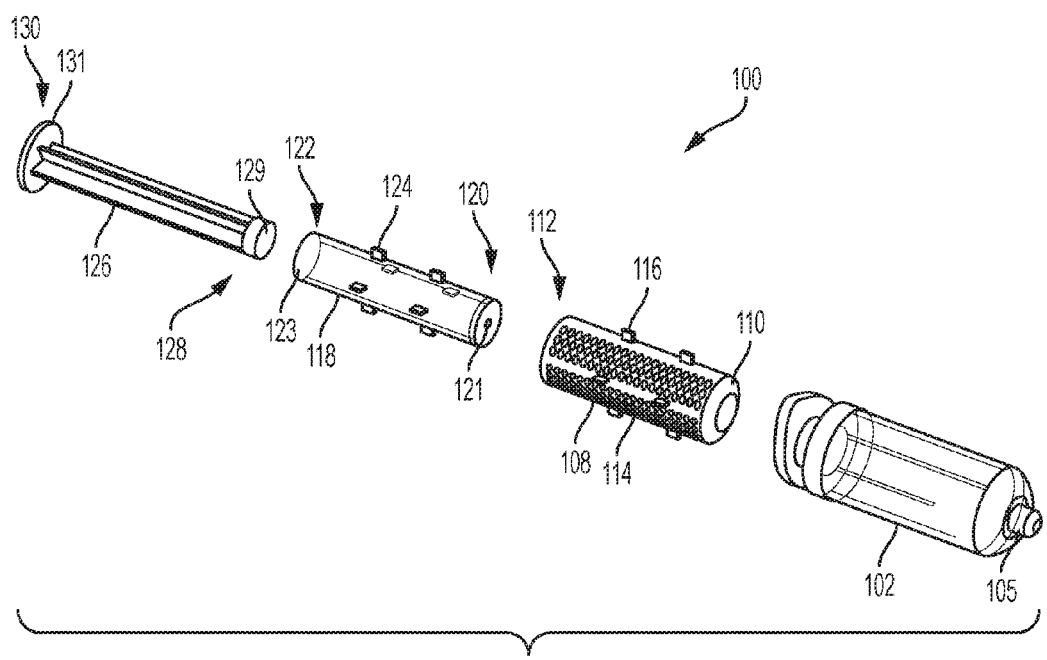
FIG. 2 is an exploded view of the binding syringe shown in FIG. 1.
Figure 3:
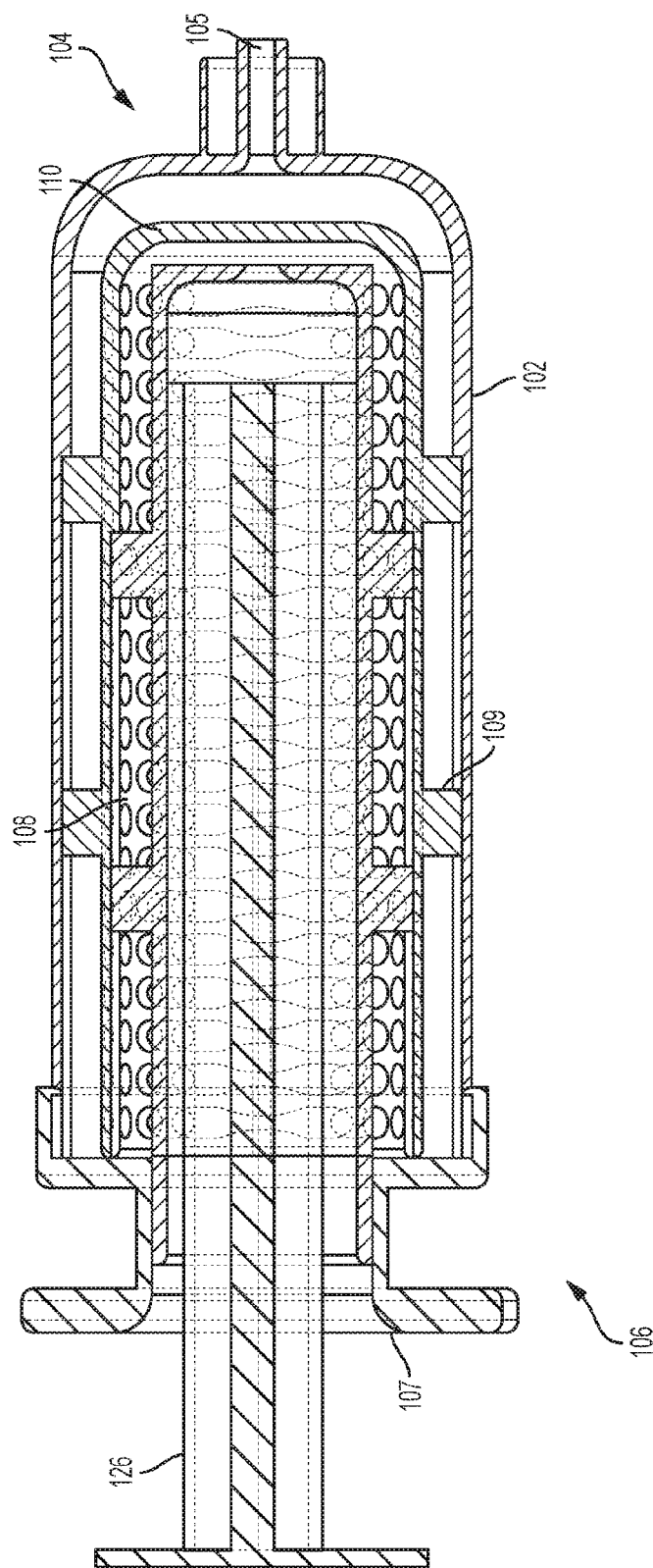
FIG. 3 is a cross-sectional view of the binding syringe shown in FIG. 1.

Referring to FIGS. 1-3, the binding syringe 100 includes an outer body 102. The outer body 102 has a proximal end 104 and a distal end 106. The proximal end 104 includes an opening 105 through which a fluid can be taken in or extruded. The distal end 106 of the outer body 102 includes an opening 107 for receiving a middle chamber there through, as described in detail below.

Figure 4:
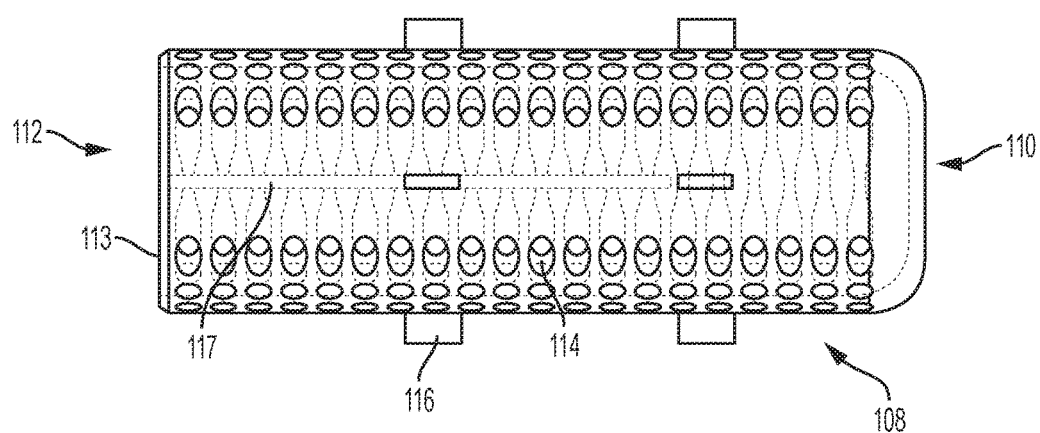
FIG. 4 is a close-up view of a middle chamber of a binding syringe.

The binding syringe 100 further includes a middle chamber 108 positioned within the outer body 102. The middle chamber 108 has a proximal end 110 and a distal end 112, as best seen in FIG. 4. The proximal end 110 is closed and the distal end 112 has an opening 113. The middle chamber 108 further includes a plurality of pores 114. The pores 114 may vary in size. Depending on the size of the pores 114, different products or components of biological fluid can be retained. For example, the pores 114 can have a molecular weight cut off (MWCO) of about 15 kiloDaltons (kD) to retain products such as IL-1β and TNF-α. In another example, the pores 114 can have a MWCO of about 40 kD to retain products such as MMP-1. In some examples, the pores 114 can have a MWCO of about 10 kD to about 1,000,000 kD (for example a MWCO of about 10, 50, 100, 1,000, 5,000, 10,000, 20,000, 30,000, 40,000, 50,000, 60,000, 70,000, 80,000, 90,000, 100,000, 250,000, 500,000, 750,000, 1,000,000 kD or more) or any range between about 10 and 1,000,000 kD. For example, the MWCO of the pores can be between about 5 and 15 kD, between about 10 and 20 kD, between about 10 and 40 kD, or between about 20 and 50 kD. In other examples the size of the pores 114 can range from about 0.00001 µm to about 100 µm, (e.g. about 0.00001, 0.0001, 0.001, 0.01, 0.1, 1.0, 10, 25, 50, 75, 100 µm or more (or any range between about 0.00001 and 100 µm). It should be understood that other size pores can also be used to retain other products. It should be noted that the pores 114 do not allow large particles to pass through. Thus, as explained further with respect to FIG. 6 below, the fluid taken in or extruded from the opening 105 in the proximal end 104 of the binding syringe 100 cannot flow through the pores 114.

In another example, the pores 114 of the middle chamber 108 can be coated with one or more ligands, such as antibodies, proteins, nucleic acids, drugs, and chemicals. The ligand will bind to specific components of the biological fluid. For example, proteins such as IL-1β (i.e., IL-1F2), IL-1a (i.e., IL-1F1), IL-6, TNF-α, IFN-γ, matrix metalloproteinase (MMP) (e.g., MMP1, MMP2, MMP3, MMP7, MMP8, MMP9, MMP10, MMP11, MMP12, MMP13, MMP14, MMP15, MMP17, MMP19, MMP20, MMP21, MMP23A, MMP23B, MMP24, MMP25, MMP26, MMP27, and MMP28), anabolic proteins, proteins beneficial to healing, Transforming Growth Factor-β (TGF-β), Vascular Endothelial Growth Factor (VEGF), Insulin-like Growth Factor (IGF), Platelet-Derived Growth Factor (PDGF), Epidermal Growth Factor (EGF), and IL-1RA can be immobilized to a syringe via one or more ligands. Ligands for IL-1β include, for example, IL-1R1 receptor, IL-1R2 receptor, IL-1RA, and antibodies specific for IL-1β such as canakinumab. Ligands for IL-1α include for example, IL-1R1 receptor, IL-1R2 receptor, and antibodies specific for IL-1α. Ligands for IL-6 include for example, IL-6 receptor, and antibodies specific for IL-6 such as tocilizumab and siltuximab. Ligands for TNF-α include, for example, TNF receptor type 1, TNF receptor type 2, entanercept, and antibodies specific for TNF-α such as infliximab, adalimuab, and certolizumab. Ligands for IFN-γ include, for example, IFN-γ receptor 1, IFN-γ receptor 2 and antibodies specific for IFN-γ. Ligands for matrix metalloproteinases include, for example, antibodies such as doxycycline, marimastat, and antibodies specific for MMP1, MMP2, MMP3, MMP7, MMP8, MMP9, MMP10, MMP11, MMP12, MMP13, MMP14, MMP15, MMP17, MMP19, MMP20, MMP21, MMP23A, MMP23B, MMP24, MMP25, MMP26, MMP27, and MMP28. Ligands for TGF-β include, for example, TGF-β receptor and anti-TGF-β antibodies, such as fresolimumab. Ligands for VEGF include, for example, VEGF receptor and anti-VEGF antibodies like aflibercept, bevacizumab, ranibizumab. Ligands for IGF (e.g., IGF-1 and IGF-1) include, for example, IGF-1R, IGF2-R, IGF-1 binding proteins (e.g., IGFBP1, IGFBP2, IGFBP3, IGFBP4, IGFBP5, IGFBP6, and IGFBP7), and anti-IGF antibodies like anti-IGF-1 and anti-IGF-2 antibodies. Ligands for PDGF include, for example, PDGFA, PDGFB, PDGFC, PDGFD, PDGFR-α, PDGFR-β, and anti-PDGF antibodies. Ligands for EGF include, for example, EGFR and anti-EGF antibodies. Ligands that bind to specific components of the biological fluid can be immobilized to the pores 114 of the middle chamber 108 via any method in the art. For example, noncovalent immobilization techniques, covalent immobilization techniques, secondary antibody-mediated immobilization techniques, immobilization via binding proteins, and Protein A or G-mediated immobilization can be used to immobilize one or more ligands to the syringe.

Protein A, a surface protein of *Staphylococcus aureus*, or Protein G, a recombinant streptococcal protein, Fc region specific antibodies, and various recombinant proteins have a high affinity for and binding specificity towards the Fc region of a broad range of mammalian immunoglobulins (Ig) and can be used to immobilize ligands to the syringe.

NHS ester-activated resins react with primary amines and can be used to immobilize protein ligands to the syringe. In an example, the syringe can be aldehyde-activated (using e.g., AminoLink™ Coupling Resin), azlactone-activated (using e.g., a durable polyacrylamide-like resin formed by co-polymerization of acrylamide with azlactone (e.g., UltraLink™ Biosupport)), carbonyl diimidazole (CDI) activated, maleimide-activated, Iodoacetyl-activated, pyridyl disulfide activated, hydrazide-activated, or carboxyl-activated. In an embodiment, once activated, one or more ligands can be immobilized to the syringe.

Referring back to FIG. 4, the middle chamber 108 can further include one or more tabs 116. The tabs 116 facilitate alignment and placement of the middle chamber 108 during assembly of the binding syringe 100. The tabs 116 mate with corresponding recesses 109 (shown in FIG. 3) located within an interior surface of the outer body 102. It should be understood that any other type of known alignment mechanism can be used to align the middle chamber 108 with the outer body 102.

Figure 5:
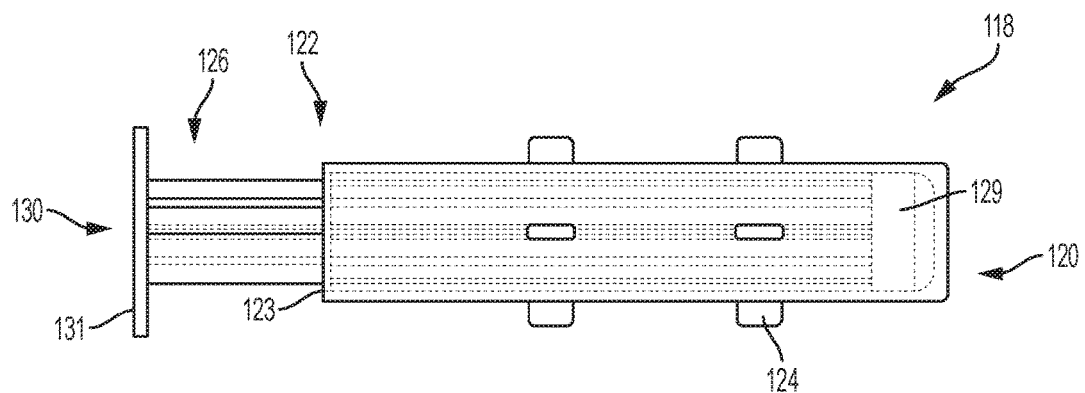
FIG. 5 is a close-up view of an inner chamber and plunger of the binding syringe.

The binding syringe 100 further includes an inner body 118 positioned within middle chamber 108. The inner body 118 is shown in detail in FIG. 5. The inner body 118 has a proximal end 120 and a distal end 122. The proximal end 120 has an opening or hole 121 (shown in FIG. 2) through which fluid can flow. The distal end 122 has an opening 123 to receive a plunger, which is described in detail below.

In one example, the inner body 118 can also include one or more tabs 124. The tabs 124 facilitate alignment and placement of the inner body 118 during assembly of the binding syringe 100. The tabs 124 mate with corresponding slits or openings 117 (shown in FIG. 4) located in the middle chamber 108. It should be understood that any other type of known alignment mechanism can be used to align the inner body 118 with the middle chamber 108.

Referring again to FIGS. 1-3, the binding syringe 100 further includes a plunger 126, which is configured to move back and forth within the inner body 118. The plunger 126 has a proximal end 128 and a distal end 130. The proximal end 128 can be formed as a stopper 129. The distal end 130 can include a flange 131 to facilitate gripping of the plunger 126 by a user. The plunger 126 can be moved within the inner body 118 by a user to operate the binding syringe 100.

As mentioned above, the binding syringe 100 can be used to extract unwanted products or components from a biological fluid such as blood, serum, PRP, autologous serum, BMC, BMA, BMMC, SVF from adipose tissue, amniotic fluid, synovial fluid, and other enriched or concentrated biological fluids. Before use, the binding syringe 100 is assembled by inserting the middle chamber 108 into the outer body 102, then inserting the inner body 118 into the middle chamber 108, and finally inserting the plunger 126 into the inner body 118. As mentioned above, tabs 116 facilitate alignment of the middle chamber 108 into the outer body 102, and tabs 124 facilitate alignment of the inner body 118 into the middle chamber 108.

Figure 6:
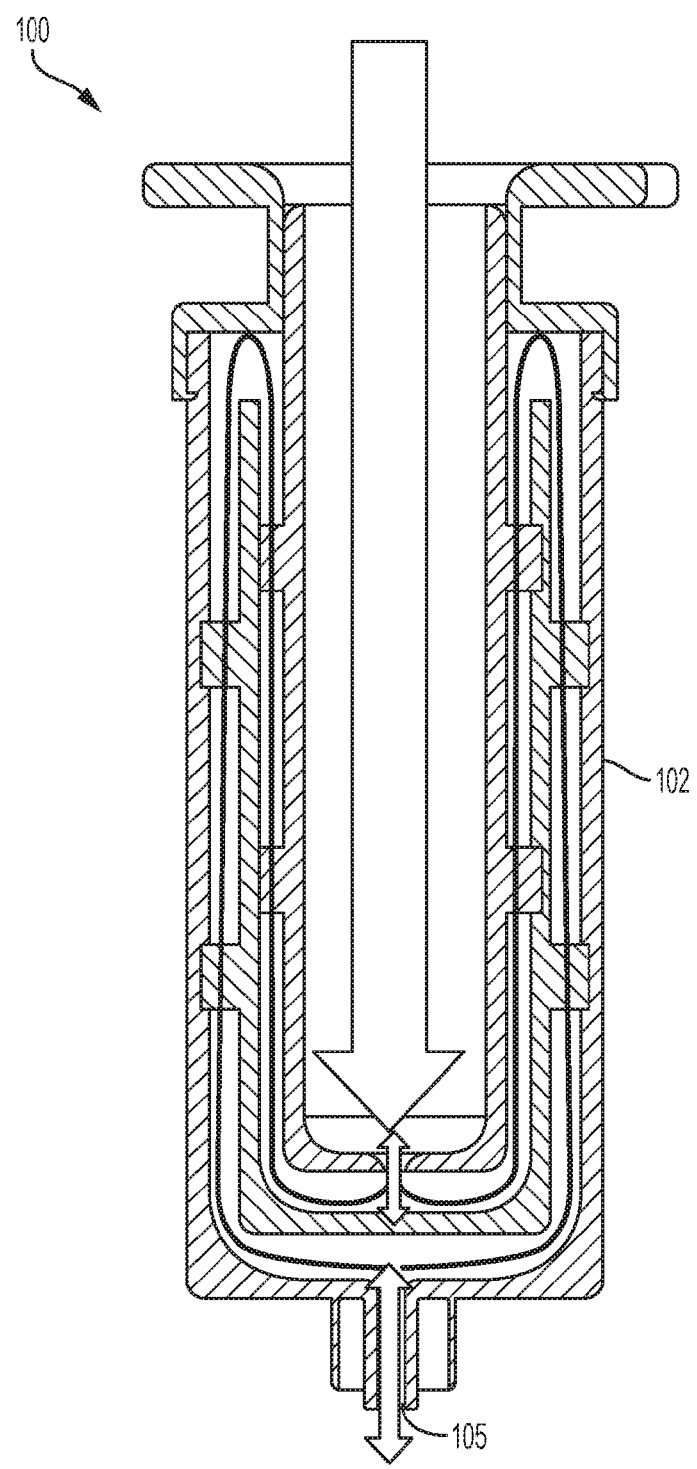
FIG. 6 shows an example flow path of a binding syringe.

In use, the plunger 126 is pulled out of the inner body 118, and biological fluid is taken from the patient or a container and into the opening 105 in the outer body 102. The extracted fluid flows around the middle chamber 108 and into the space between the middle chamber 108 and the inner chamber 118. FIG. 6 shows the fluid flow path within the binding syringe 100. As the fluid passes around the middle chamber 108, certain components of the biological fluid will bind to the pores 114 in the middle chamber 108. Alternatively, as described above, certain components can bind to an antibody or other ligand immobilized on the middle chamber 108. As explained above, the fluid does not flow through pores 114 in the middle chamber 108, but rather flows around the middle chamber, as shown in FIG. 6. Fluid can be pumped back and forth around the middle chamber 108 by oscillating (i.e., pushing and pulling back and forth on) the plunger 126 to increase contact with the middle body 108, which will in turn increase the likelihood of binding.

Once the certain products have been removed from the biological fluid, the remaining treated biological fluid can then be returned to the body or a container for later use by the user pushing on the plunger 126 to insert the wanted/desired portion of the fluid (i.e., the treated biological fluid) back into the patient or container.

In another aspect, the binding syringe 100 can be used to extract anabolic proteins, proteins beneficial to healing, or other beneficial or desirable components from a product. Examples of proteins that are beneficial to healing include IL-1RA, TGF-β, VEGF, IGF (IGF-1, IGF-2), PDGF and EGF. The beneficial proteins bind to one or more ligands immobilized to the pores 114 of the middle chamber 108. After immobilization of the beneficial proteins, the beneficial proteins can be released from the syringe via, for example, ultrasonication or high frequency vibration and collected. The beneficial proteins can then be used to treat a patient. The beneficial proteins or other products can then be injected back into the patient, or can be saved for use at a later time.

The binding syringe 100 is disposable and can be discarded after use. The binding syringe 100 can be constructed of a polymeric material, such as polysterene, for example. It should be understood that the binding syringe 100 can be constructed of other suitable materials.

The biological fluid prepared by a binding syringe can be used, for example, in the treatment of soft tissue injury or damage. In an embodiment, the treated biological fluid prepared by a binding syringe can be used for administration via injection into a ligament, tendon, muscle, bone, connective tissue, bone, cartilage, or joint space.

In one aspect, about 0.1, 0.5, 1, 5, 10, 15, 20, 25 mL or more treated biological fluid derived by the methods described herein can be administered to a subject. A subject can be a mammal. A mammal can be, e.g., human, canine, feline, equine, or bovine.

In another aspect, treated biological fluid derived by the methods described herein can be administered to a subject not undergoing surgery. Treated biological fluid can be administered by, for example an injection, directly into cartilage, ligament, tendons, connective tissue, bone, soft tissue, muscle, or a joint space of a subject not undergoing surgery. For example, a subject having chronic tendinopathies (e.g., Achilles tendinosis, lateral/medial epicondylitis, plantar fasciitis, patellar tendinopathy) can be administered treated biological fluid via injection into a tendon. In one example, a subject having chondral injuries and early or advanced osteoarthritis can be administered treated biological fluid.

In another aspect, treated biological fluid derived by the methods described herein can be administered to a subject during surgery. Treated biological fluid can be administered during surgery to repair soft tissue damage or injury, such as for a ligament (e.g., anterior cruciate ligament, medical collateral ligament, etc.), cartilage (e.g., meniscus, labrum, etc.), connective tissue, muscle, joint, or tendon (e.g., Achilles tendon). Treated biological fluid can also be administered during surgery to promote bone repair (e.g., patella, tibia, femur, humerus, etc.). Treated biological fluid can also be used to treat ischemia, ischemic stroke, heart injury or damage, muscle injury or damage, osteoarthritis, rheumatoid arthritis, and other diseases. Treated biological fluid can be administered directly to soft tissue or to the joint space (e.g., shoulder, knee, ankle, wrist, hip, etc.).

In yet another aspect, treated biological fluid derived by the methods described herein can be administered to a subject with a neuropathy (e.g., peripheral neuropathy).

In the methods described herein, treated biological fluid administered to a subject can be autologous. For example, the treated biological fluid administered to a subject can be allogeneic.

In yet another aspect, treated biological fluid derived by the methods described herein can be administered in combination with one or more specific growth factors. Growth factors include, but are not limited to, platelet-derived growth factor (PDGF), fibroblast growth factor (FGF), TGF-β (transforming growth factor-β), epithelial growth factor (EGF), and vascular endothelial growth factor (VEGF). Growth factors can be added to the treated biological fluid or administered separately simultaneously or sequentially at about 0.001, 0.01, 0.1, 1.0, 10, 100 or more ng/mL.

In another example, treated biological fluid derived by the methods described herein can be administered in combination with bone marrow concentrate (BMC), bone marrow aspirate (BMA), or lipoaspirate. About 1, 2, 5, 10, 15, 20, 25 mL or more BMC, BMA, or lipoaspirate can be added to the treated biological fluid or separately administered simultaneously or sequentially.

In yet another embodiment, treated biological fluid derived by the methods described herein can be administered in combination with stem cells. For example, the treated biological fluid can be administered with mesenchymal stem cells or bone marrow stem cells. About 0.1, 0.5, 1, 2, 5, 10, 15, 20, 25 mL or more mesenchymal stem cells or bone marrow stem cells can be added to the treated biological fluid or separately administered simultaneously or sequentially.

In an embodiment the treated biological fluid derived by the methods herein can be administered directly from a binding syringe or a second container to the patient through an injection kit attached to the binding syringe or second container. For example, the binding syringe can be connected to an injection kit and the treated biological fluid can be directly administered to a patient.

The various considerations set out in respect of the treated biological fluid in the preceding paragraphs, and the relevant features relating to administration are all, except for where the context requires otherwise, applicable to the corresponding medical uses of the treated biological fluid as defined herein.

While a number of exemplary aspects have been discussed above, those of skill in the art will recognize that still further modifications, permutations, additions and sub-combinations thereof of the disclosed features are still possible. It is therefore intended that the following appended claims and claims hereafter introduced are interpreted to include all such modifications, permutations, additions and sub-combinations as are within their true spirit and scope. As used herein, the term "about" in association with a numerical value means that the value varies up or down by 5%. For example, for a value of about 100, means 95 to 105 (or any value between 95 and 105).

The invention claimed is:

1. A binding syringe comprising:
   an outer body having a distal end and a proximal end, the proximal end having an opening for extracting biological fluid;
   a middle chamber configured to be positioned within the outer body, the middle chamber having an open distal end, a closed proximal end, and an outer surface including a plurality of pores, the pores being configured to retain products from the biological fluid extracted by the outer body;
   an inner body configured to be positioned within the middle chamber, the inner body including a proximal end having a first opening and a distal end having a second opening through which the biological fluid flows; and
   a plunger configured to be positioned within the inner body, the plunger being configured to move within the inner body, thereby pushing and pulling the biological fluid in and out of the second opening in the inner body;
   wherein a flow path is created through the opening in the proximal end of the outer body, around the middle chamber, and through the first opening in the inner body.

2. The binding syringe of claim 1 wherein middle chamber is coated with one or more ligands.

3. The binding syringe of claim 1 wherein the plurality of pores have a molecular weight cut off of about 10 kD to about 1,000,000 kD.

4. The binding syringe of claim 1 wherein the plurality of pores are about 0.00001 μm to about 100 μm in size.

5. The binding syringe of claim 1 wherein the middle chamber includes one or more tabs.

6. The binding syringe of claim 1 wherein the inner body includes one or more tabs.

7. The binding syringe of claim 1 wherein the binding syringe is constructed of a polymeric material.

8. A method of extracting components of a biological fluid comprising:
   placing a binding syringe into a patient or a container of biological fluid, the binding syringe comprising:
      an outer body having a distal end and a proximal end, the proximal end having an opening for extracting the biological fluid;
      a middle chamber configured to be positioned within the outer body, the middle chamber having an open distal end, a closed proximal end, and an outer surface including a plurality of pores, the pores being configured to retain components from the biological fluid extracted by the outer body;
      an inner body configured to be positioned within the middle chamber, the inner body including a proximal end having a first opening and a distal end having a second opening through which the fluid flows; and
      a plunger configured to be positioned within the inner body, the plunger being configured to move within the inner body;
   actuating the plunger to extract the biological fluid from the patient or container, wherein a flow path is created through the opening in the proximal end of the outer body, around the middle chamber, and through the first opening in the inner body; and
   wherein the biological fluid flows within the flow path; and
   oscillating the plunger to bind the components of the biological fluid to be extracted to the pores in the middle chamber, and preserving remaining biological fluid within the flow path.

9. The method of claim 8 further comprising injecting the remaining biological fluid into a patient or container.

10. The method of claim 8 wherein the middle chamber is coated with one or more ligands.

11. The method of claim 8 wherein the components are unwanted components.

12. The method of claim 11, wherein the unwanted components are proteins selected from the group consisting of IL-1β, IL-1α, IL-6, TNF-α, IFN-γ, matrix metalloproteinase (MMP), and combinations thereof.

13. The method of claim 12, wherein the MMP comprises MMP1, MMP2, MMP3, MMP7, MMP8, MMP9, MMP10, MMP11, MMP12, MMP13, MMP14, MMP15, MMP17, MMP19, MMP20, MMP21, MMP23A, MMP23B, MMP24, MMP25, MMP26, MMP27, MMP28, or combinations thereof.

14. A method of extracting components of a biological fluid comprising:
   placing a binding syringe into a patient or a container of biological fluid, the binding syringe comprising:
      an outer body having a distal end and a proximal end, the proximal end having an opening for extracting fluid;
      a middle chamber configured to be positioned within the outer body, the middle chamber having an open distal end, a closed proximal end, and an outer surface including a plurality of pores, the pores being configured to retain components from biological fluid extracted by the outer body;

an inner body configured to be positioned within the middle chamber, the inner body including a proximal end having a first opening and a distal end having a second opening through which the fluid flows; and a plunger configured to be positioned within the inner body, the plunger being configured to move within the inner body;

actuating the plunger to extract the biological fluid from the patient or container, wherein a flow path is created through the opening in the proximal end of the outer body, around the middle chamber, and through the first opening in the inner body; and wherein the biological fluid flows within the flow path;

oscillating the plunger to bind the components of the biological fluid to be extracted to the pores in the middle chamber; and subjecting the middle chamber or binding syringe to ultrasonication or high frequency vibration such that the components of the biological fluid to be extracted are removed from the middle chamber.

15. The method of claim 14, wherein the middle chamber is coated with one or more ligands.

16. The method of claim 14, wherein the components of the biological fluid comprise Transforming Growth Factor-β (TGF-β), Vascular Endothelial Growth Factor (VEGF), Insulin-like Growth Factor (IGF), Platelet-Derived Growth Factor (PDGF), Epidermal Growth Factor (EGF), IL-1RA, or combinations thereof.

* * * * *